Figure 1:
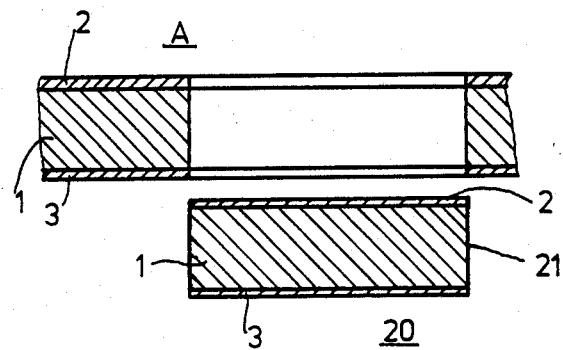

United States Patent [19]

Hamed et al.

[11] Patent Number: 4,823,595
[45] Date of Patent: Apr. 25, 1989

[54] PROCESS AND APPARATUS FOR MEASURING THE EQUILIBRIUM MOISTURE IN A HYGROSCOPIC, LAMINAR MATERIAL WHICH IS COATED ON BOTH SIDES

[75] Inventors: Saleman Hamed, Leichlingen; Jörg M. Söder, Cologne, both of Fed. Rep. of Germany

[73] Assignee: Agfa-Gevaert AG, Leverkusen, Fed. Rep. of Germany

[21] Appl. No.: 101,997

[22] Filed: Sep. 28, 1987

[30] Foreign Application Priority Data

Oct. 10, 1986 [DE] Fed. Rep. of Germany ....... 3634518

[51] Int. Cl.⁴ ............................................. G01N 21/00
[52] U.S. Cl. ............................................ 73/73; 73/76; 324/58.5 A; 83/98; 72/254
[58] Field of Search ............... 73/73, 76, 29, 49.3, 73/45.4; 324/65 R, 61 R, 58.5 R, 58.5 A, 58.5 B, 58.5 C; 177/210 FP; 340/602, 605; 116/206; 72/254, 257; 83/348, 660, 98; 30/358

[56] References Cited

U.S. PATENT DOCUMENTS

| | | | |
|---|---|---|---|
| 3,512,003 | 5/1970 | Berry et al. | 73/73 |
| 4,297,874 | 11/1981 | Sasaki | 73/73 |
| 4,380,169 | 4/1983 | Graham | 73/73 |
| 4,418,596 | 12/1983 | Garrocho | 83/98 |
| 4,485,284 | 11/1984 | Pakulis | 73/76 X |
| 4,499,708 | 2/1985 | Lewandowski et al. | 72/254 X |
| 4,534,250 | 8/1985 | Garrocho | 83/98 |
| 4,548,072 | 10/1985 | McAndless | 73/73 |
| 4,600,879 | 7/1986 | Scully et al. | 324/58.5 A |
| 4,716,360 | 12/1987 | Pakulis | 324/58.5 A |

Primary Examiner—William M. Shoop, Jr.
Assistant Examiner—Paul Ip
Attorney, Agent, or Firm—Connolly & Hutz

[57] ABSTRACT

In a process for measuring the equilibrium moisture in hygroscopic, laminar material coated on both sides, preferably in raw paper coated on both sides used as support for a photographic paper, by determining the relative moisture of the air in contact with the material, samples are removed from the material by a process which forms cut surfaces on the material and are introduced into a container which can be sealed off against the outer atmosphere, and after establishment of the equilibrium moisture in this container the relative moisture of the air contained therein is measured.

8 Claims, 2 Drawing Sheets

PROCESS AND APPARATUS FOR MEASURING THE EQUILIBRIUM MOISTURE IN A HYGROSCOPIC, LAMINAR MATERIAL WHICH IS COATED ON BOTH SIDES

This invention relates to a process for measuring the equilibrium moisture in a hygroscopic, laminar material coated on both sides, preferably in the support of a photographic paper, by determining the relative moisture of the ambient air which is in moisture exchange with the material. The invention also relates to an apparatus for carrying out this process.

The supports used for the photographically active emulsion layers of colour photographic and black and white photographic paper usually consist of raw paper with a weight per unit area of about 50–300 g/m² and a thickness of about 80 to 130 μm. This raw paper is covered on both sides with a coating of polymer, preferably polyethylene, 20 to 40 μm in thickness. These surface coatings of the support prevent rapid absorption of water by the raw paper when the photographic paper is subsequently developed after photograhic exposure.

For producing the photographic paper, the photographically active emulsion layers are poured on the above mentioned support so that the lowermost layer of the packet of layers cast on the support is in contact with the upper coating of the paper support. The layer packet is solidified after it has been cast on its support and the cast web of paper is dried to a certain, predetermined moisture level before it is rolled up on a spool and made ready for use.

If the moisture content is too high, the separate turns of the rolled up length of film may stick together. This may give rise to mechanical damage or electrostatic charges and flash exposures. If the moisture content is too low even by a small amount, this also may lead to the accumulation of charges and flash exposures. The photographic properties are also considerably influenced by the water content, in particular the sensitometric properties of the photographic paper and its durability.

The water content of the photographic paper is determined to a considerable extent by the moisture in the paper core of the support, especially as the polyethylene coating does not completely prevent exchange of moisture between the paper core of the support and the layer packet on the support in the course of prolonged storage.

The following factors are to be taken into consideration.

The photographic properties of the photographic paper are determined, firstly, by the moisture content of the packet of emulsion layers which have a thickness of only a few μm. In the production of photographic paper, the solidification and drying process in the paper casting machines is adjusted to dry the photograhpic layers to a certain equilibrium moisture level in the region of 40 to 60% relative humidity. When the finished photographic paper is made up into rolls, however, and especially if it is stored over prolonged periods, a moisture equilibrium is established between the support and the packet of emulsion layers since if there is any difference in the moisture content between the two, the moisture levels slowly become equalised by the diffusion of water through the polyethylene layer of the support. This equilibrium may take days or weeks to become established, depending on the thickness of the polyethylene layer. The comparatively thick raw paper, which constitutes the core of the support, has a water content of 4 to 8% which is in most cases considerably higher than the water content of the emulsion layers. The water content of the raw paper should therefore also be adjusted to the desired moisture content of the end product.

In order to ensure this, it is not only desirable but important to measure the water content of the coated raw paper of the support as a measure of quality control when producing photographic paper.

This may be carried out by determining the equilibrium moisture content in the raw paper of the support. This equilibrium moisture content is defined as the moisture equilibrium which is established with a hygroscopic material, in this case the raw paper, at a constant temperature within a closed system. It is well known that in the state of equilibrium, the sorption isotherms represent the relationship between the absolute water content of the hygroscopic material and the equilibrium moisture so that the sorption isotherms can be used to determine the absolute water content of the hygroscopic material from the measured value of the equilibrium moisture. See, for example, Stefan Gal, "Die Methodik der Wasserdampf-Sorptionsmessungen", Springer-Verlag, 1967.

It is already known to measure the equilibrium moisture in the raw paper of the photographic paper support by means of contact sensors which are placed in hermetically sealed contact with the raw paper. They measure by means of an atmospheric moisture sensor the equilibrium moisture which is established in the closed air volume above the paper after a certain length of time. This method of measurement cannot always be used for supports which are coated with polyethylene on both sides since the diffusion of water through the polyethylene layer from the raw paper is so slow that it takes a very long time before a state of equilibrium is reached under the measuring probe placed on the polyethylene layer.

To overcome this disadvantage it has already been attempted in the case of thicker supports to tear parts of the polyethylene layers from the raw paper so that the contact sensor can be placed in direct contact with the raw paper. This method has the disadvantage, however, that if certain areas of the polyethylene layer are torn off the raw paper, the paper rapidly changes its moisture content due to exchange of water with the ambient air by diffusion. This procedure therefore requires great care and experience on the part of the operator. Moreover, reliable measurements cannot be obtained if the raw paper has a weight per unit area of less than about 120 g/m² since it is then not possible to tear off the covering layer without damaging the raw paper.

The possibility has therefore already been considered of measuring the moisture content of the raw paper of the support by drying out the support completely and measuring the weight loss due to the moisture loss. This method, however, takes several hours and is therefore not a practicable proposition as a method of production and quality control.

It is at this point that the invention sets in. Its object is to provide a simple but reliable and relatively rapid method of determining the moisture content of the raw paper in a support coated on both sides, regardless of the thickness of the paper and therefore also applicable to supports having an extremely thin paper core.

The process solves this problem by the features of claim 1 of the attached patent claims. Further features of the invention will be found in the subordinate claims.

The process according to this invention has the advantage that it provides reliable measurements within a short time. This is due to the fact that the moisture content of the material between the surface coatings can diffuse rapidly out through the cut surfaces of the samples of material so that a moisture equilibrium can rapidly be established inside the closed container in which the samples are placed. Another advantage is that the interior of the samples of material are virtually excluded from contact with the ambient air by their surface coatings.

The moisture equilibrium in the container is established all the more rapidly the higher the ratio of the total sum of all the cut surfaces of the samples in the container to the volume of the container. Experiments have shown that when the container has a volume of about 100 ml and about 30 to 50 samples are introduced in the form of cutout discs about 5 mm in diameter, a state of moisture equilibrium can be established in the container within about five minutes. The material consisted of a polyethylene coated raw paper intended as support for photographic paper. The equilibrium mositure in the container was established at a relative humidity of about 50% in the air in the container. Under these conditions, the influence of the atmospheric moisture originally present inside the container i.e. before introduction of the samples of material, was negligible.

By virtue of its simplicity, the process according to the invention can be carried out by relatively unskilled operators without any loss of accuracy in the measuring results obtained.

Figure 2:
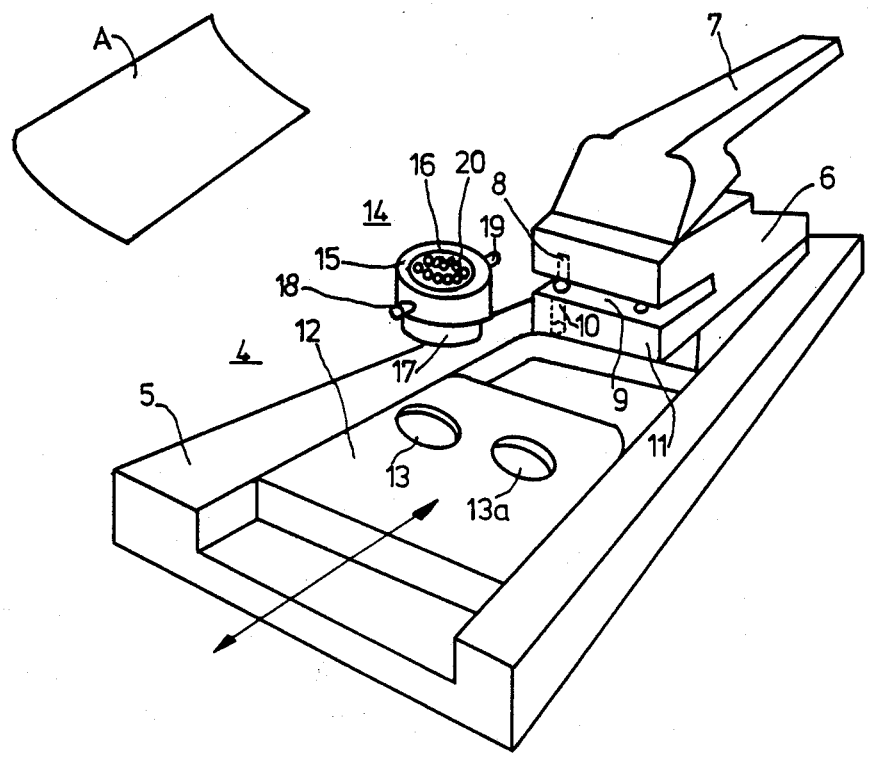
Figure 3:
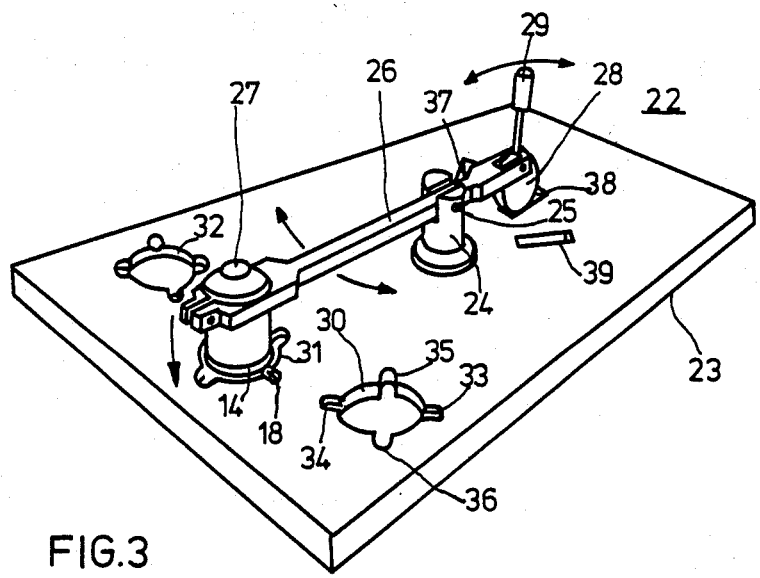
Figure 4:
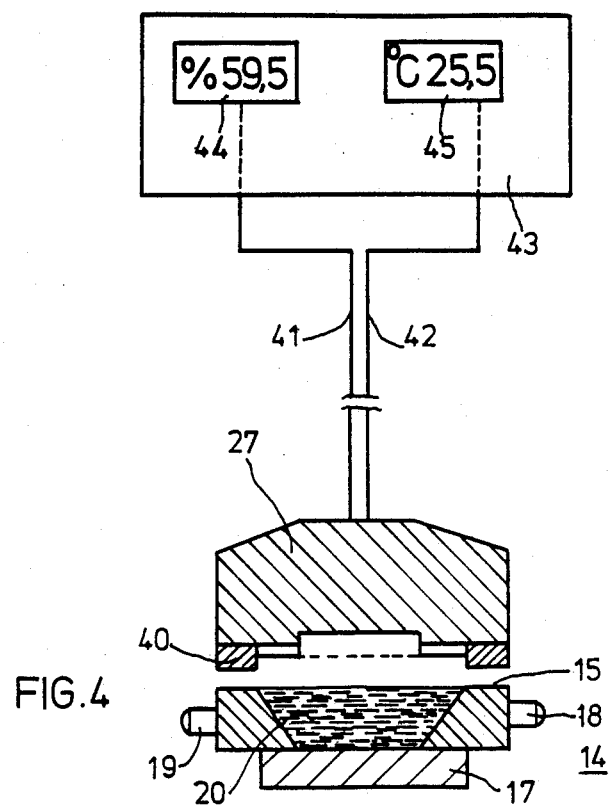

An example of the invention is described below with reference to the accompanying drawings, in which FIG. 1 represents a cross section through the support of a photographic paper on a highly enlarged scale, FIG. 2 shows an apparatus for punching out samples of material from the support shown in FIG. 1 and for collecting these samples in a container, FIG. 3 shows a measuring device with the container of FIG. 2 seen from above, and FIG. 4 represents a section through the container and measuring sensor with indicator attached.

FIG. 1 is a cross sectional view of a section of a sheet-like support A for photographic paper on a highly enlarged scale. The support consists of a laminar core 1 of raw paper coated on its upper and lower surfaces with layers 2, 3 of polyethylene.

The punching apparatus 4 shown in FIG. 2 comprises a frame 5 on which a conventional punch 6 is mounted. This punch has a hand operated rocking lever 7 by which a punching ram 8 can be moved perpendicularly to its longitudinal axis by way of a transmission (not shown) so that when the lever 7 is pressed down, the ram moves through a slot 9 which holds the material into a bore 10 in the base 11 of the punch. The bore 10 extends through the whole wall thickness of the projecting base 11 and is therefore open at the bottom.

A carriage 12 is displaceable in the frame 5 of the punching apparatus 4. This carriage 12 has an opening 13 for the insertion of a sample container 14. Additional openings 13A for additional sample containers may be provided in the carriage 12 if the apparatus 4 has additional punching rams.

The sample container 14 has an annular wall 15 forming an inner chamber 16, a base 17 and diametrically projecting mounting pins 18, 19. The container 14 may be inserted by its base 17 into the opening 13 of the carriage 12 of the punching apparatus.

When samples of material are to be punched out of the support A the empty sample container 14 is inserted in the opening 13 of the carriage 12 and moved with the carriage until it is situated under the bore 10 of the punch 6. A piece of the support A is then introduced into the slot 9 of the punch 6. The required number of circular discs 20 are punched out of the support A by the operator repeatedly moving the rocking lever 7 and at the same time displacing the support A in the slot 9. One of these disc shaped samples of material 20 with cylindrical cut surface 21 is shown on a highly enlarged scale in FIG. 1.

The discs of sample material 20 punched out of the support A in the slot 9 successively drop through the bore 10 into the interior 16 of the sample container 14 in which they are loosely stacked.

When a sufficient number of samples 20 have been punched out and collected in the container 14, the carriage 12 is moved back and the container 14 is removed from the punching apparatus and placed in the measuring device 22 of FIG. 3.

The measuring device 22. comprises a base plate 23 on which a column 24 is mounted to be rotatable about its longitudinal axis. A two-armed lever 26 mounted on the column 24 is rotatable about its axis 25. A moisture measuring sensor 27 is firmly clamped to one end of this lever while the other end of the lever carries a cam 28 with operating lever 29.

As both the column 24 and the lever 26 are rotatably mounted, the measuring sensor 27 can be pivoted in two degrees of freedom, both parallel to the base plate 23 and in planes perpendicular to the base plate.

Three circular openings 30, 31, 32 are situated in the range of horizontal rotation of the measuring sensor 27. Each of these openings has recesses 33, 34 for mounting means and recesses 35, 36 for handles. When the sample container 11 has been removed from the punching apparatus 4, it may be placed selectively into one of the openings 30, 31 or 32 with the mounting pins 18, 19 of the container 14 being fitted into the recesses 33, 34 of the opening so that the container 14 can be tilted on its mounting in the opening 30 or 31 or 32.

Diametrically opposite the openings 30, 31 and 32 for the sample container 14 and situated on the other side of the mounting column 24, the base plate 23 has recesses 37, 38 and 39 designed to receive the lower part of the cam 28.

By rotation of the lever 26 the measuring sensor 27 can be positioned over the sample container 14 inserted in one of the openings 30, 31 or 32 and can be lowered onto its annular wall 15. Since the measuring sensor 27 has an annular elastic seal 40 and the sample container 14 can be tilted in the opening 30, 31 or 32 about an axis perpendicular to the longitudinal axis of the lever 26 due to the arrangement of the recesses 33 and 34, the interior 16 of the sample container 14 is hermetically sealed off against the outer atmosphere when the operating lever 29 is placed vertically so that the measuring sensor 27 is pressed down against the container 14 by the eccentric action of the cam 28.

Since the measuring device 22 has several openings 30, 31, 32, sample containers 14 from several punching apparatus 4 can be placed in the measuring device 22 at the same time so that the sensor 27 can measure samples from different containers 14 in rapid succession when it is rotated horizontally. The measuring arrangement may also be calibrated to standard values by placing a container similar to the sample containers 14 but containing a saturated solution of a calibrating salt in one of the openings 30, 31 or 32.

The measuring sensor 27 is of known construction and has therefore not been illustrated in detail in the drawings. In the embodiment shown in FIG. 4 the moisture measuring sensor 27 is additionally equipped with a temperature measuring sensor (not shown). The measuring sensors are connected to an indicator device 43 by two leads 41, 42. The indicator device has an indicator area 44 for indicating the relative atmospheric moisture in the measuring space 16 and an indicator area 45 for indicating the temperature in that space. The circuit arrangement of the measuring and indicator device is basically known and therefore not shown in detail in the drawing.

The sample containers 14 may be closed by a lid (not shown) if considerable time is liable to elapse between introduction of the samples into the container and the moisture measurements in the measuring device 22. The sample containers 14 may also have additional devices for keeping the temperature in the space 16 constant if the temperature in the space 16 is liable to fluctuate considerably without a thermostat due to the conditions of the surroundings. The moisture measuring sensor 27 may be fixed in the container 14.

Instead of using the punching apparatus 4 shown in FIG. 2, other apparatus of known type may be used for obtaining samples 20 from the support A with suitable cut surfaces 21, e.g. a willowing machine. The samples 20 need not be in the form of discs but may be strips etc.

The process according to the invention and the apparatus according to the invention are suitable not only for determining the moisture content of the raw paper of polyethylene laminated supports for photographic paper but also for determining the moisture content of other hygroscopic laminar materials which have surfaces suitably coated to prevent rapid penetration of moisture from baths or the like.

Two sheets of drawings attached.

We claim:

1. A process for measuring equilibrium moisture in hygroscopic, laminar material having each side coated adaptable as a photographic paper support
   comprising measuring the relative moisture of air contiguous to a laminar material coated on each side and having hygroscopic properties,
   including the steps of forming cut surfaces in said material, removing samples from said cut material, introducing said samples into a container, sealing the container containing said samples from ambient atmosphere,
   establishing an equilibrium moisture within said sealed container,
   and measuring the relative moisture in said sample containing sealed container.

2. Process according to claim 1, characterized in that the samples of material which have cut surfaces are obtained from the laminar material by a punching or cutting device.

3. Process according to claims 1 or 2, characterized in that the temperature in the container is kept constant.

4. In a device for measuring equilibrium moisture in a hygroscopic, laminar material having each side coated
   means for forming cut surfaces of the laminar material,
   a punch for producing samples of the cut material,
   a container for containing said samples having sealing means to establish equilibrium moisture with said samples in said container,
   and a moisture measuring sensor associated with the container.

5. Apparatus according to claim 4 characterized in that the measuring sensor (27) can be placed on the container (14).

6. Apparatus according to claim 5, characterized in that the measuring sensor is mounted on a rocking arm (26) in whose range of rotation are situated several openings (30, 31, 32) for receiving sample containers (14) for alternate attachment of the measuring sensor (27) thereto.

7. A device according to claim 4, characterized in that the moisture measuring sensor (27) is combined with a temperature measuring sensor.

8. A device according to claim 4 characterized in that the container has a device for keeping the temperature constant.

* * * * *